United States Patent [19]
Schiek, Sr.

[11] Patent Number: 5,046,488
[45] Date of Patent: Sep. 10, 1991

[54] SUPPORT BELT FOR THE LUMBAR VERTEBRAE

[76] Inventor: James W. Schiek, Sr., 513 B Saratoga Ave., Fond du Lac, Wis. 54935

[21] Appl. No.: 491,349

[22] Filed: Mar. 9, 1990

[51] Int. Cl.⁵ .............................................. A61F 5/02
[52] U.S. Cl. .................................... 128/78; 2/338; 2/44; 272/143
[58] Field of Search ............ 128/78, 24 R, 100.1, 128/101.1, 102.1, 112.1, 89 R, 876; 2/44, 338, 339, 312; 450/2; 272/143, 123

[56] References Cited

U.S. PATENT DOCUMENTS

| | | | |
|---|---|---|---|
| 75,737 | 3/1868 | Crocker | 128/100.1 |
| 882,181 | 3/1908 | Thomas | 272/143 |
| 2,115,879 | 10/1939 | Kaplan . | |
| 2,181,689 | 11/1939 | Bell | 128/78 |
| 2,543,416 | 2/1951 | Mergehenn | 128/102.1 |
| 3,116,735 | 1/1964 | Geimer . | |
| 3,521,623 | 7/1970 | Nichols et al. . | |
| 3,554,190 | 1/1971 | Kaplan . | |
| 3,568,670 | 3/1971 | Gaylord, Jr. | 128/78 |
| 3,603,316 | 9/1971 | Lehman | 2/338 X |
| 3,605,731 | 9/1971 | Tigges . | |
| 3,888,245 | 6/1975 | Berntson et al. | 272/143 X |
| 4,080,962 | 3/1978 | Berkeley . | |
| 4,175,553 | 11/1979 | Rosenberg | 2/44 X |
| 4,193,395 | 3/1980 | Gruber . | |
| 4,475,543 | 10/1984 | Brooks et al. . | |
| 4,572,167 | 2/1986 | Brunswick . | |
| 4,627,109 | 12/1986 | Carabelli et al. | 2/44 |
| 4,747,399 | 5/1988 | Glomstead | 2/339 X |
| 4,768,499 | 9/1988 | Kemp | 128/78 |
| 4,833,730 | 5/1989 | Nelson | 2/44 |
| 4,836,194 | 6/1989 | Sebastian et al. | 128/78 |
| 4,907,576 | 3/1990 | Curlee | 128/78 |
| 4,964,401 | 10/1990 | Taigen | 272/143 X |
| 4,968,027 | 11/1990 | Anderson | 2/338 X |
| 4,991,573 | 2/1991 | Miller | 128/78 |

Primary Examiner—Richard J. Apley
Assistant Examiner—Linda C. M. Dvorak
Attorney, Agent, or Firm—Andrus, Sceales, Starke & Sawall

[57] ABSTRACT

A support belt adapted to encircle the waist, comprising a unitary structure of pliable, nonelastic material, and having a back section for spanning the lumbar vertebrae. Strap means extend obliquely from the back section to form a belt, when considered in elevational side view, of a truncated configuration.

10 Claims, 3 Drawing Sheets

SUPPORT BELT FOR THE LUMBAR VERTEBRAE

FIELD OF THE INVENTION

This invention relates to a back support device. In its more specific aspect, this invention relates to a support belt for the waist area of the human body. Still more specifically, this invention relates to a belt for supporting the lumbar vertebrae of the spinal column to prevent injury.

BACKGROUND OF THE INVENTION AND PRIOR ART

The prior art discloses a wide variety of support devices such as belts, braces, garments, etc., which commonly are useful for therapeutic or orthopedic rehabilitation following injury or surgery. A number of support devices of this type are designed to encircle the wearer at the waist, and to provide a supportive or corrective force to the lumbar region and sacrum region of the back where injury is most likely to occur. When such a support belt is firmly tensioned about the wearer's waist, the back musculature and spine are indirectly held in an arbitrary position with a limited freedom of movement. Further, belts of this type are, in the vast majority of cases, constructed of an elastic fabric or webbing. The elasticity may be unilalteral, typically in the horizontal plane with reference to the position of the wearer, or bi-directional so that the fabric can stretch in both directions, i. e., horizontally and vertically.

A support device or belt comprising an elastic fabric is advantageous in that it readily conforms to the contour of the wearer's body and provides comfort to the wearer after injury or surgery. However, an elastic belt will not sufficiently constrain the musculature nor vertebrae to protect these body parts from injury.

An elastic belt for support of the spinal column, especially in the region of the dorsal vertebrae and sacrum, is disclosed in U.S. Pat. No. 3,605,731 to Tigges. The rear inner side of the belt is provided with an array of support elements which have a bowed middle part that overlies the vertebrae. The support elements are carried on a metal strip which is bent to conform to the natural contour of the spinal column, thereby imparting an hour glass shape to the belt. According to the Tigges patent, the support elements massage the muscles of the spinal column, and hold the abdomen in the correct place for exerting the requisite internal pressure against the spinal column.

In U.S. Pat. Nos. 3,554,190 and 2,115,879 there are disclosed support garments comprising a plurality of elastic panels stretchable in a body encircling direction only. The panel sections are joined by cross-stitching, which permits one panel to move or stretch relative to an adjacent panel. In this manner, the garment conforms to the contour of the body.

Support belts have been provided With a pocket in the rear section. A thermoformable material that can be molded into a support panel at an elevated temperature is inserted.into the pocket and molded directly to the body contour. Upon cooling to room temperature, the panel exhibits strength and resiliency. An orthopedic device utilizing this feature is disclosed in U.S. Pat. No. 4,572,167 Brunswick. The device comprises an elastic web, strap means for tightening the device, and a pocket for receiving the molding material which is shaped to the contour of the body part. According to Brunswick, this device provides for a quick, easy and comfortable means in fitting the brace to the patient. A similar device is shown in U.S. Pat. No. 4,475,543 to Brooks et al.

The emphasis for these devices as shown in the prior art is therapeutic, that is for rehabilitation after injury or surgery. A person engaged in sports, vehicular driving, or in an occupation requiring lifting or sitting for long perids of time, needs proper back support and protection against injury. A back support belt that is elastic will provide comfort after injury, but will not provide a satisfactory constraint of any duration on the back musculature which, for example, is important to one who is lifting weights whether as a sport or in the course of their occupation.

It is the purpose of this invention to provide a back support belt that is prophylactic, and especially useful for an active person needing protection against injury.

SUMMARY OF THE INVENTION

Broadly, the present invention provides a back support device for the lumbar vertebrae of the human spinal column. The lumbar vertebrae in the human spinal column consists of five vertebrae, and extend from the fifth lumbar vertebra just above the dorsal to the twelfth thoracic vertebra. The support device comprises a belt having a back section or zone and laterally extending strap members formed integrally with the back section, and is adapted to encircle the waist area of a human body. The back section and strap means or members are formed of a pliable, nonelastic material, and a tightening means firmly straps the belt around the wearer's waist. The back section has a vertical dimension that spans the region of the lumbar vertebrae, at least in whole or in part, and is adapted to bear firmly, when the belt is tightened about the waist, upon the lumbar vertebrae and back musculature. It will be observed that the belt device comprised of the back section or zone and strap means is essentially a unitary or single piece and not in panel sections or parts, whether lateral or transverse, but it is understood that the belt may have a body facing surface or fabric and an exterior surface or fabric, and padding which may be of variable thickness, and further the belt may include stitching or the like to provide reinforcement and prevent unraveling.

In accordance with the invention, the strap means extends obliquely from the back section with respect to the vertical axis of the back section. It is preferable that this oblique angle be at least about four degrees from the normal plane to the vertical axis. Thus, when the belt is viewed from a side elevation, such as in a girdling position on a human body, the belt forms a truncated cone. This configuration provides a natural taper for the waist area of the body, and because the fit is firm to the contour of the body waist, the belt provides support and protection to the lumbar region.

In a preferred embodiment of the invention, the back or rear section has incorporated therein a flexible or pliable panel member. Although the panel member may be fabricated of any suitable flexible material, it has been found that a plastic member, such as a polyolefin, e. g. polyethylene, polyvinyl resins such as polyvinyl chloride which may contain a plasticizer, and the like, is particularly desirable and convenient to use. The panel member, which preferably is substantially rectangular, has a vertical dimension or width sufficient to span some or substantially all of the lumbar vertebrae, and a horizontal dimension or length sufficient to span the lumbar region and, if desired this horizontal dimension may be greater to span a part or substantially all of the lateral lumbar region. The panel member is inserted in the back section between the body facing surface and exterior surface, and, if desired, is affixed in position as by stitching to prevent any displacement, shifting or movement.

A still further preferred embodiment provides that each strap means adjacent the back or rear zone, has a taper that converges toward the terminus of the strap. The taper extends for a short distance only, and preferably at both the top and bottom as viewed in a vertical or wearing position. In this manner, the strap means has a width that is less than the width (vertical dimension) of the back section. Hence, the belt, and in particular, the strap means is contoured over the iliac crest of the pelvis thereby enhancing both the fit and comfort.

DETAILED DESCRIPTION AND PREFERRED EMBODIMENTS

Figure 1:
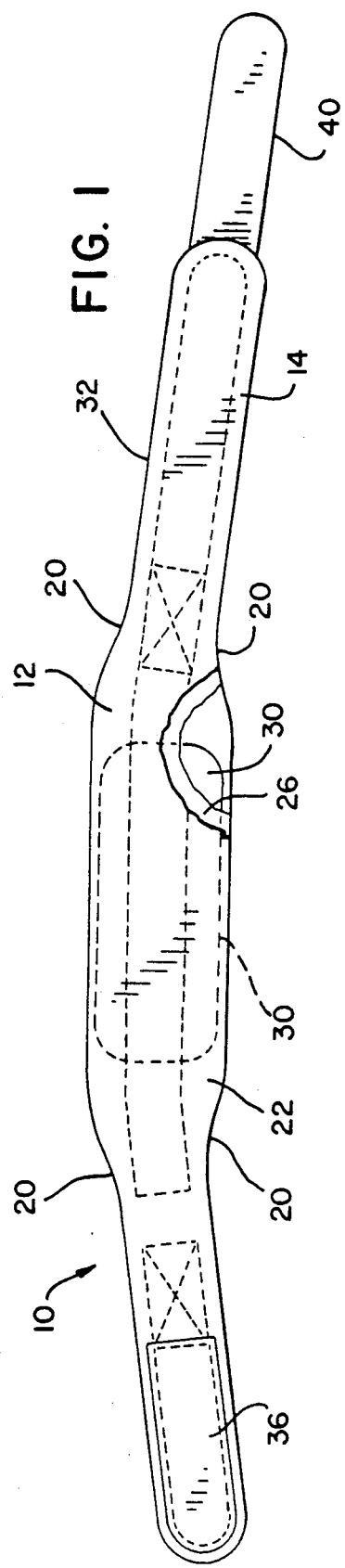
FIG. 1 is a side elevational view of the support device of this invention, as viewed from the body facing side, and is partly in fragmentary to show certain details.
Figure 2:
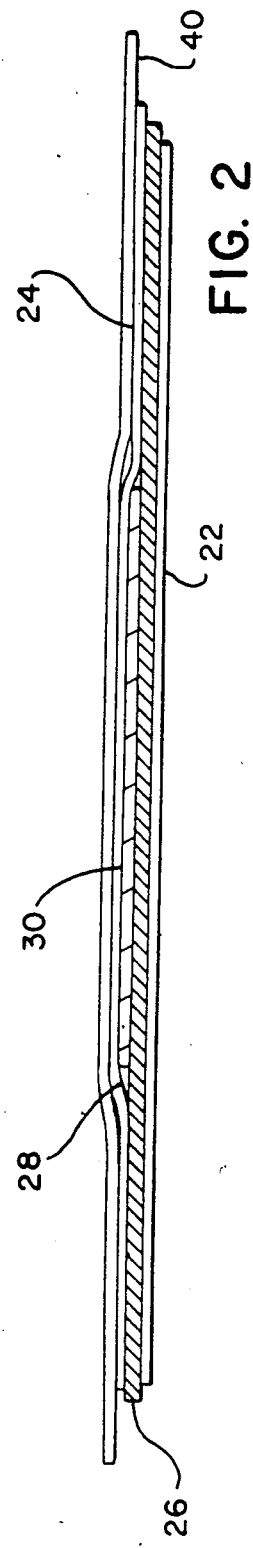
FIG. 2 is a horizontal sectional view of the support device of FIG. 1.
Figure 3:
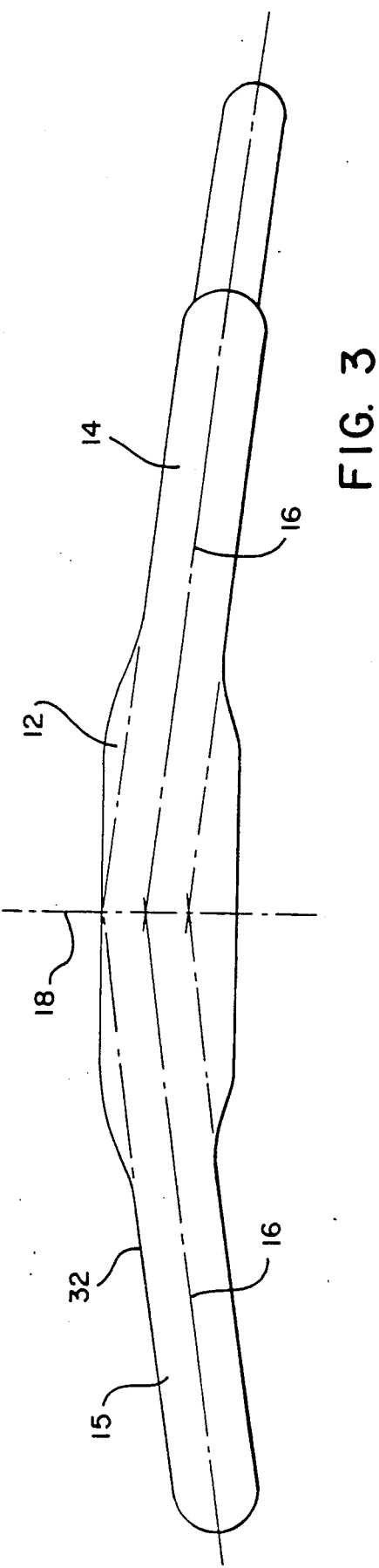
FIG. 3 is a side elevational view of the support device of this invention as viewed from the body facing side.
Figure 9:
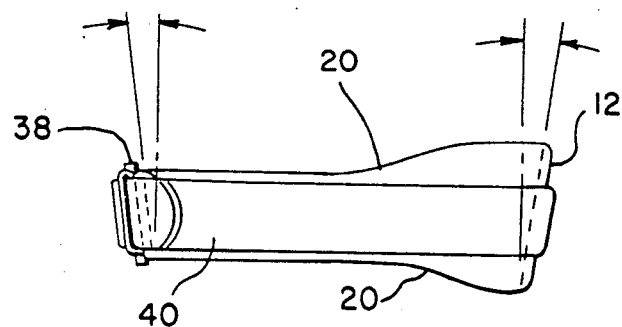
FIG. 9 is an elevational view from the side as in a wearing position with the belt being buckled to show the frusto-conical configuration of the device.

Referring to the drawings wherein like reference numerals refer to similar parts throughout, there is shown a support device of the present invention as indicated by the numeral 10 providing a back support for the lumbar vertebrae of the human spinal column. The support device comprises a belt support adapted to encircle the waist area of the human body, and when tightened about the waist, provides firm support to the lumbar region, as explained more fully below. As shown in FIGS. 1 through 3, the belt 10 comprises a back section or zone 12, and first and second strap means 14 and 15 formed integrally with the back section and extending laterally therefrom. Each strap means extends obliquely from the back section with respect to the horizontal plane drawn normal to the vertical axis of the back section, as shown at arrows X. With reference in particular to FIG. 3, this oblique angle is shown in phantom lines, wherein oblique lines 16 drawn as the longitudinal axis of each strap means converge at the central vertical axis 18 of the back section. This angle is small, desirably at least about 4 degrees, but sufficient to form the belt as a frusto-conical configuration when viewed from the side in a wearing positions shown if FIG. 9, whereby the circumference at the top is greater than the circumference at the bottom The oblique angle may range from about 4 to 25 degrees, and preferably is about 15 degrees. The taper provided by such an inverted frusto-conical shape or truncated cone is especially advantageous in that the taper conforms closely to the contour of the waist of the wearer, as will be more apparent from the complete description of this detail hereinbelow.

The belt comprising the back zone and strap means is an integrally fabricated piece or a unitary structure formed of a pliable, nonelastic fabric or material. This type of structure is advantageous in that it eliminates the need of providing for individual fabric panels or sections that are joined at a seam as by stitching, which can be more costly, produces a weak zone with use, and causes an uncomfortable gathering or bunching at the seam. The back section is substantially rectangular, and has a vertical dimension or width that spans some or substantially all of the lumbar vertebrae, preferably all five lumbar vertebrae from the sacrum at the lower end of the spinal column to the twelfth thoracic vertebra. The horizontal dimension or length of the back section is sufficient to span the lumbar region on each side of the spinal column, and more preferably to span part or all of the lateral lumbar region at the small of the back. Therefore, when the belt is drawn tightly about waist, the back section is applied firmly to the lumbar vertebrae and back musculature. These dimensions will depend upon the size, but for purposes of illustration, for an average belt the horizontal dimension may be about 12 to 18 inches and the vertical dimension about 3 to 6 inches.

The strap means is generally of smaller width than the back section not only for the purpose of economizing on material but more importantly in providing for a more comfortable fit in the waist. In order to accomplish this reduced width for the strap means, the strap means, at the imagined dividing line between the back section and strap means, is tapered inwardly at 20, with reference to the horizontal axis, at both the top and bottom and converges in a direction toward its terminus. Where desired, the bottom only need be tapered, and in the preferred embodiment, there is provided a concave taper. Generally, the taper extends for not more than about one-fourth the length of each strap means, and more preferably from about one-tenth to one-fourth the length. There is shown a strap means with top and bottom boundaries, beyond the taper, that are substantially parallel, but where desired, both boundaries may be convergent.

As best seen in FIG. 2, the belt has a body facing fabric or webbing 22 and an exterior fabric or webbing 24. These fabrics may be of the same or different material, and fabrics for structures of this type are well known and readily available. Most typically, the fabric is a plastic material such as nylon, polyester, acrylic, or a polyolefin. The body facing fabric is coated or treated with a moisture resistant composition such as, by way of example, "NEOPRENE" manufactured by ITT Corporation, thereby rendering this surface substantially impervious to moisture or body perspiration. In order to provide additional comfort to the wearer, padding 26, such as closed cell foam or sheet foam, is placed intermediate the body facing fabric and the exterior fabric. Pocket 28 is formed between the padding 26 and exterior fabric 24, which is adaptable for accommodating panel member 30. This panel member is formed of flexible or pliable material, preferably a plastic such as polyethylene, and has dimensions sufficient to span two or more, preferably at least three, of the lumbar vertebrae and back musculature as described above with reference to the back section. In the preferred embodiment, the panel member 30 is affixed to the belt, as by stitching, in order to prevent displacement or shifting. Where desired, however, the pocket dimensions may be carefully measured to hold snugly the panel member thereby obviating any need for stitching. The marginal edges of the belt, i. e., back section and strap means, are folded at edges 32 and stitched in order to provide strength and prevent unraveling. The belt may be stitched along the length and or width in order to conjoin the components in order to reinforce the structure, prevent shifting during normal use, and to prevent unraveling.

Figure 4:
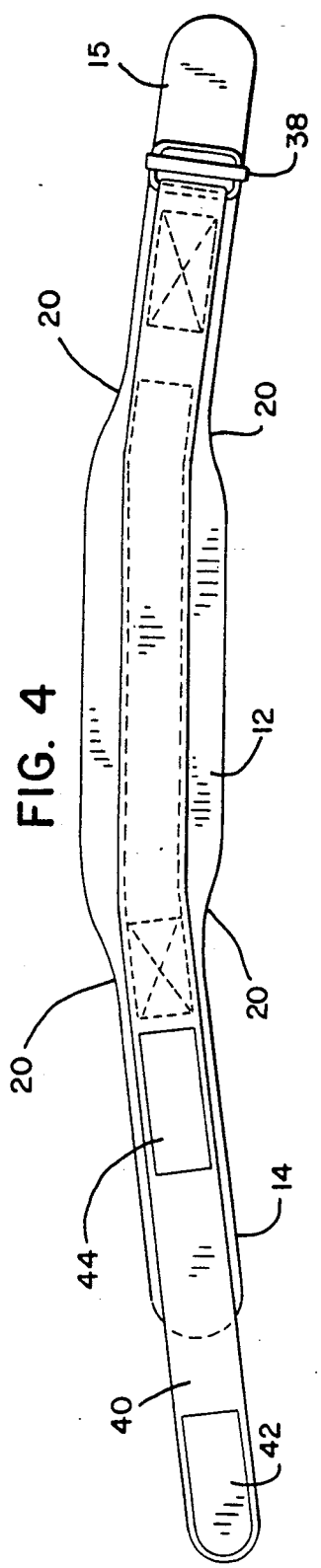
FIG. 4 is a side elevational view of the support device of FIG. 1 as viewed from the exterior side to illustrate the angle of the strap members relative to the vertical axis of the back section.
Figure 5:
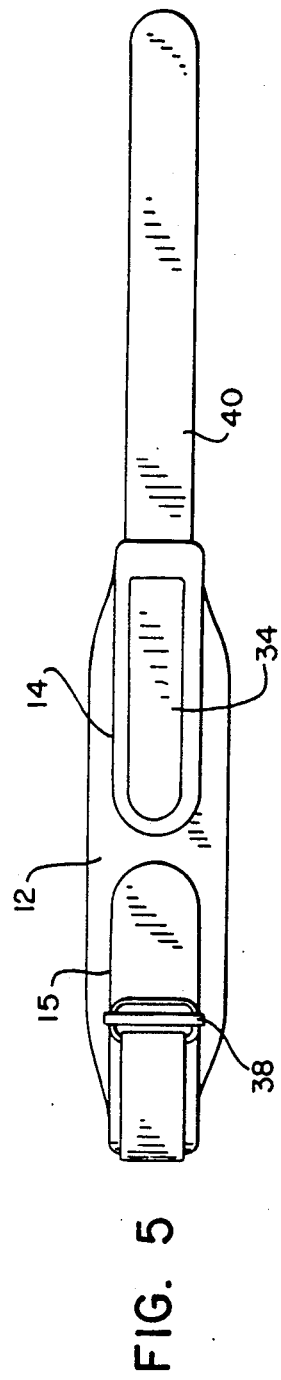
FIG. 5 is front elevational view showing the support device in a partially closed position.
Figure 7:
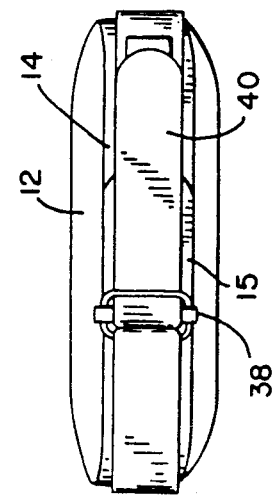
FIG. 7 is a front elevational view illustrating the closure assembly in its final position as when the belt is tightened about the waist of the wearer.
Figure 6:
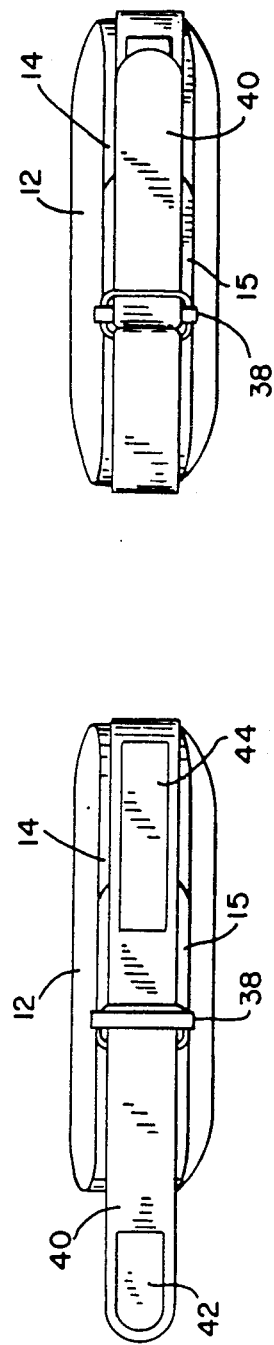
FIG. 6 is front elevational view showing the strap members overlapped to provide a fastening mechanism between mating surfaces.
Figure 8:
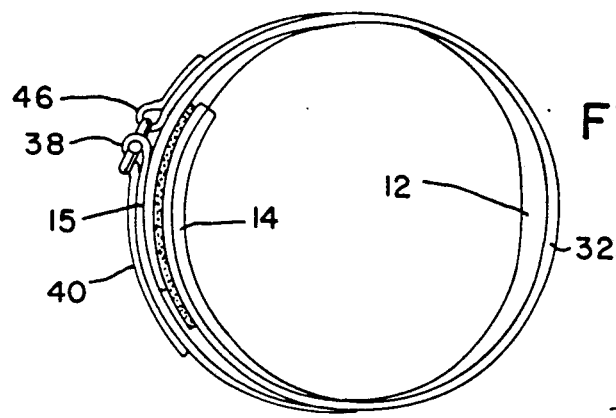
FIG. 8 is a diagramatic plan view of the belt of FIG. 1.

A closure assembly adapted to secure the two strap means 14 and 15 together and provide for tightening the belt firmly about the waist of the wearer is illustrated in FIGS. 5 to 7. The closure means comprises a first fastening means for joining the first and second strap members 14 and 15. These strap members may be joined in overlapping relation by utilizing a hook and loop type fastener such as the VELCRO brand manufactured by VELCRO Industries, B. V. fastener. Strap member 14 is provided on its exterior or outside, surface 24 and near the terminus thereof with one-half of the VELCRO fastener 34, and strap member 15 is provided on its interior or body facing surface 22 and near its terminus with the complementary half of VELCRO fastener 36. When the belt is fitted about the waist of the wearer, the strap members 14 and 15 are brought into overlapping relation thereby bringing the VELCRO fastener strips into contact and fastening the strap means about the waist. This first or preliminary fastening step holds the strap members in place and permits the wearer to make any adjustments, and further when the belt is fully secured, provides extra holding action. In order to provide a more firm tightening action to the back section and panel member, the closure assembly also includes a slide bar buckle 38 and tensioning strap 40. As shown, in FIG. 4 tensioning strap 40 is affixed at one end to the outer surface of the belt, desirably to strap means 14, and extends longitudinally therewith beyond the terminus of said strap means. The outer surface of this tensioning strap 40 is provided with complementary VELCRO fastening elements 42 and 44. The opposite end of strap 40 is folded at the terminus to provide loop 46 (FIG. 8) for accommodating buckle 38. Tensioning strap 40 is drawn through the buckle, and then folded back to bring the free end bearing VELCRO fastening element 42 into overlapping relation with the complementary Velcro element 44, and on contact fastens the tensioning strap. The slide bar buckle and tensioning strap provide for infinite adjustment so that the belt can be tensioned to any desired position about the waist area of the wearer. This buckle and strap arrangement furnishes to the wearer the tight hold, which is important in providing firm support. Thus, when the strap 40 is tightened through the buckle 38, the back section bears firmly against the back of the wearer and the panel member 30 provides firm support to the wearer.

Figure 10:
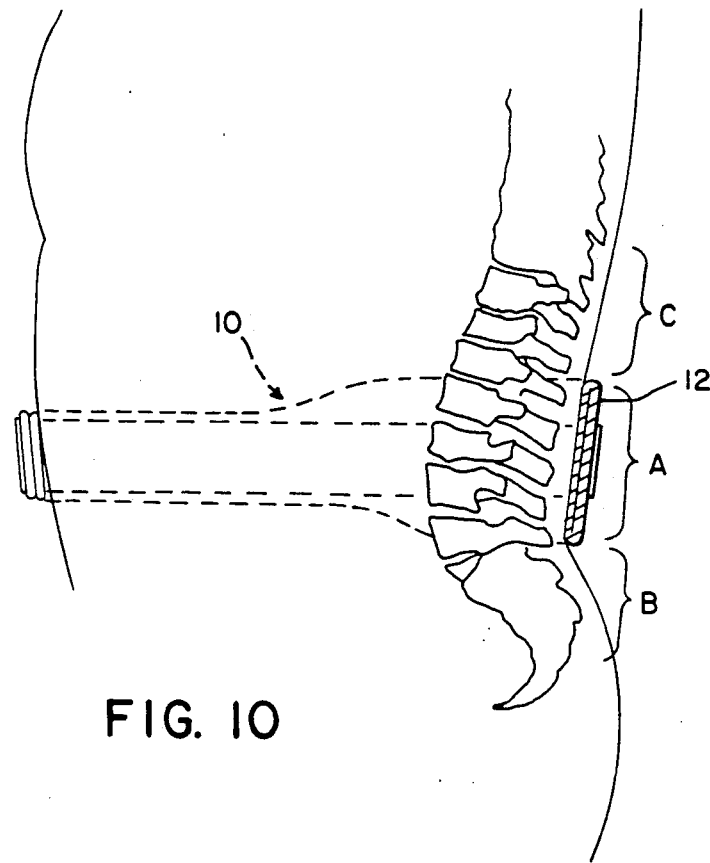
FIG. 10 is a diagramatic elevational view of a human being wearing an embodiment of the inventive device showing in phantom outline the position of spinal vertebrae and waist in relation to the support device.

The fitting of the support belt is illustrated further in FIG. 10, which is a cross-section view of the support as it is worn on the back of the wearer. When the belt has been positioned about the waist of the wearer and the closure assembly tightened, a tightening action imparted to the back panel member 30 in the rear section 12 pulls the panel member against the lumbar region for firm support. It will be observed that the back section of the belt as illustrated spans all five vertebrae of the lumbar region A. Thus, the back section extends in its vertical dimension from just above the sacrum B to the twelfth thoracic vertebra in the thoracic region C. Where desired, the back section can have a smaller vertical dimension, but it is desirable that the back section span at least about two, and more preferably three, lumbar vertebrae. Further, it will be observed that the belt does not cover the hip nor serve simply as a cosmetic girdle.

It will be observed that the support device of my invention advantageously provides for a snug fit through the lumbar lordosis or region, and that the back section with the panel member assures a firm support through contour of the lumbar lordosis. Still further, although there is the snug fit, the belt is contoured over the iliac crest of the pelvis. Hence, the belt does not limit the normal function of the lumbar spine nor of the pelvis. Because the support belt of my invention is essentially prophylactic in that it provides support and helps to prevent injury, it is particularly useful for one active in sports such as weight lifting or body building, or for one whose occupation requires heavy lifting. Another advantage of the support belt is that it increases the intra abdominal pressure, which in turn relieves pressure on the spinal disks. If there is less pressure on the spine, there is less likelihood of injuring the disks, and therefore lifting becomes safer.

The foregoing detailed description has been given for clearness of understanding only, and no unnecessary limitations should be understood therefrom, as modifications will be obvious to those skilled in the art.

I claim:

1. A support device for the lumbar vertebrae of the human spinal column, the support device of the type including a belt of a pliable, nonelastic material and adapted to encircle the waist area of the human body, the support device comprising:
    a. a back section having vertical and horizontal axes and opposed sides laterally spaced along the horizontal axis and a vertical dimension along the vertical axis spanning at least a portion of the lumbar vertebrae defining top and bottom edges and adapted to bear upon the back musculature on both sides of at least one of said lumbar vertebrae;
    b. first means including a pair of straps extending laterally outward from the opposed sides of said back section, each of said straps extending along an axis forming a downwardly acute angle with respect to the horizontal axis of said back section and having outer ends spaced outwardly from said back section; and
    c. means for securing the outer ends of said straps to one another to form a belt for encircling the human body about the waist, so that when the outer ends of said straps are secured together, said back section and straps define a tapered, truncated, conical belt, having a larger diameter at the top than at the bottom and conforming generally to the natural taper of the human body in the lumbar region.

2. A support device according to claim 1 wherein said rear section includes a flexible panel member such that upon tigthening of said belt, said panel member bears firmly against said lumbar vertebrae and back musculature.

3. A support device according to claim 2 wherein said rear section includes an exterior fabric surface and a body facing fabric surface, both of said fabric surfaces being pliable but non-elastic, and said panel member inserted between said fabric surfaces.

4. A support device according to claim 3 wherein said panel member is substantially rectangular and secured to said fabric surfaces.

5. A support device according to claim 3 wherein said panel member has a vertical dimension spanning substantially all of the lumbar vertebrae.

6. A support device according to claim 1 wherein the acute angle is at least 4 degrees.

7. A support device according to claim 1 wherein the acute angle is from about 4 and 25 degrees.

8. A support device according to claim 1, wherein the vertical dimension of said back section spans all of the lumbar vertebrae and the back musculature on both sides of said lumbar vertebrae.

9. A support device according to claim 1, further including second means including a pair of straps extending outwardly from said back section, each along an axis substantially parallel to the axis of the respective first straps, and closure means for securing and tightening said second straps for tightening the belt about the waist of the wearer for providing first support.

10. A support device according to claim 1, wherein said first strap means and said back section are of integral construction.

* * * * *

UNITED STATES PATENT AND TRADEMARK OFFICE
CERTIFICATE OF CORRECTION

PATENT NO. : 5,046,488
DATED : September 10, 1991
INVENTOR(S) : James W. Schiek, Sr.

It is certified that error appears in the above-identified patent and that said Letters Patent is hereby corrected as shown below:

Claim 9, Col. 8, Line 15:
Delete "first" and substitute therefor -- firm --.

Signed and Sealed this

Twenty-third Day of February, 1993

Attest:

STEPHEN G. KUNIN

*Attesting Officer*       *Acting Commissioner of Patents and Trademarks*